United States Patent [19]

Rogers

[11] 4,320,774
[45] Mar. 23, 1982

[54] MECHANICAL TOOTHBRUSH

[76] Inventor: Kenneth G. Rogers, 1001 Waverly Dr., Longwood, Fla. 32750

[21] Appl. No.: 143,094

[22] Filed: Apr. 23, 1980

[51] Int. Cl.³ ............................................. A45D 24/00
[52] U.S. Cl. ................................ 132/11 A; 132/84 R; 15/22 R
[58] Field of Search ............ 132/11 A, 84 R; 15/198, 15/49 R, 49 C, 80, 83, 84, 22 R, 22 B, 23

[56] References Cited

U.S. PATENT DOCUMENTS

| | | | |
|---|---|---|---|
| 585,933 | 7/1897 | Hanlon | 15/80 |
| 684,618 | 10/1901 | Schmidt | 15/80 |
| 1,097,911 | 5/1914 | Brugger | 15/80 |
| 1,791,812 | 2/1931 | Harrison | 15/49 C |
| 3,233,265 | 2/1966 | Hartmann | 15/22 R |
| 3,592,188 | 7/1971 | Barnett | 15/22 R |
| 3,903,906 | 9/1975 | Collis | 132/84 R |

Primary Examiner—G. E. McNeill
Attorney, Agent, or Firm—Duckworth, Hobby, Allen, Dyer & Pettis

[57] ABSTRACT

A brush drive unit is coupled to rotating means such as an electric motor. The brush drive unit maintains first and second belt brushes in an oval configuration and in fore and aft alignment. The brush drive unit causes the motor drive shaft to rotate the first and second belt brushes in opposing directions. The brush drive unit also includes a transmission assembly which is coupled between the motor drive shaft and the first and second belt brushes to alternately rotate the first belt brush in a first direction while maintaining the second belt brush in a substantially fixed position and for rotating the second belt brush in a second direction while maintaining the first belt brush in a substantially fixed position.

26 Claims, 5 Drawing Figures

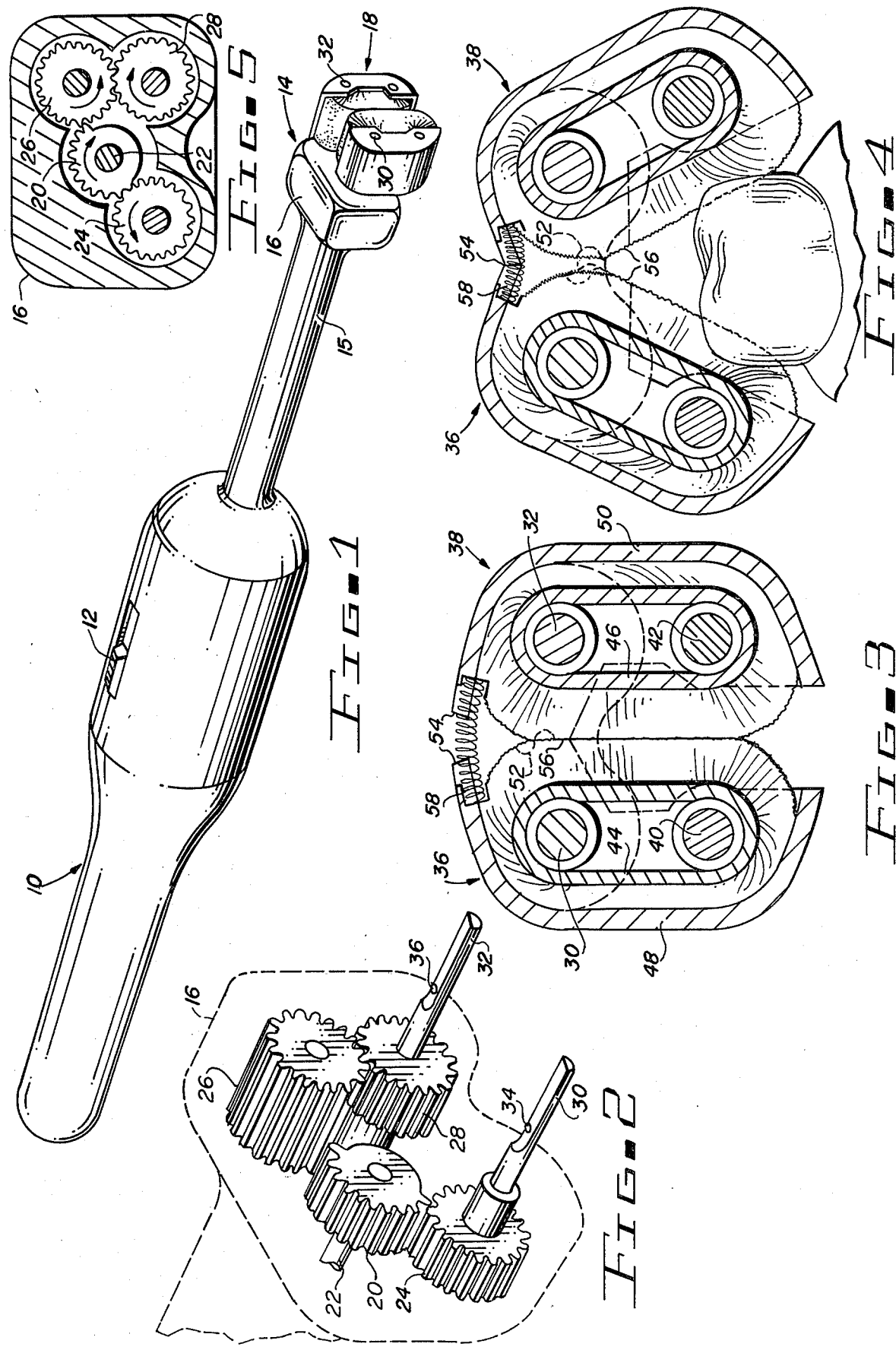

MECHANICAL TOOTHBRUSH

BACKGROUND OF THE INVENTION

1. Field of the Invention

The present invention relates to mechanical toothbrushes and more particulary to a mechanical toothbrush which includes a pair of proximately located, oval shaped belt brushes.

2. Description of the Prior Art

The prior art discloses a wide variety of mechanically actuated toothbrushes. Many of these prior art toothbrushes include paired, circular brushes which are symmetrically rotated about parallel oriented drive shafts.

U.S. Pat. No. 2,799,878 (Brousch) discloses a manually actuated mechanical toothbrush which includes a pair of brush wheels which are maintained in a spaced apart relationship by a pair of parallel oriented drive shafts. The paired drive shafts are alternately rotated in unison in first and second directions when the user compresses and then releases the telescoping drive unit positioned outside the user's mouth. U.S. Pat. No. 2,682,066 (Keeley) discloses a mechanical toothbrush which includes a spring motor which drives two parallel oriented, spaced apart drive shaft. Each drive shaft is coupled to a toothbrush head. The paired brush heads are rotated in unison alternately up and down to clean the front and rear tooth surfaces.

U.S. Pat. No. 2,655,675 (Grover) discloses a power-driven toothbrush having parallel oriented drive shafts which simultaneously rotate cylindrical brush units to clean the tooth and gum surfaces. A lip guard is provided around the outer section of each brush unit to protect the user's mouth. U.S. Pat. No. 2,655,674 (Grover) discloses a mechanical toothbrush having parallel oriented, spaced apart brush rollers. The single drive shaft includes a pair of worm gears which rotate a pair of circular brush units opposing directions.

U.S. Pat. No. 3,732,589 (Burki) discloses a mechanical toothbrush which includes a brush head which is continuously rotated in a single direction. The brush unit simultaneously contacts and brushes the upper and lower teeth and includes parallel oriented, opposing brush discs which are maintained in a spaced apart relationship by a shaft.

U.S. Pat. No. 1,225,955 (Hickman) discloses a rotary toothbrush which is manually rolled along the user's gum line. This toothbrush includes a wishbone shaped brush support. A shaft passes through a pair of disc-shaped brushes and is supported by the arms of the wishbone brush support.

U.S. Pat. No. 2,282,700 (Bobbroff) discloses a mechanical toothbrush having a motor driven eccentric weight which vibrates the toothbrush brush head. U.S. Pat. No. 2,932,835 (Everett) discloses a manually actuated toothbrush having three independently rotatable, cylindrically configured brush units.

U.S. Pat. No. 2,798,237 (Grover) discloses a mechanical toothbrush having a rotatable, semi-circular brush unit and a semi-circular lip guard. U.S. Pat. No. 2,184,850 (Schloss) discloses a mechanical toothbrush having a rotary shaft which causes the toothbrush bristles to vibrate. An alternative embodiment rotates the brush section of the toothbrush.

U.S. Pat. No. 3,677,264 (Brockman) discloses a manually operated tooth-brush which includes opposed, conical rubber rollers with corrugated side walls. Toothpaste in injected from the handle mounted toothpaste supply tube through passageways in the rollers into the mouth of the user.

SUMMARY OF THE INVENTION

The present invention contemplates a mechanical toothbrush includingg means for rotating a drive shaft. First and second loop-shaped belt brushes are provided. Brush drive means is coupled to the rotating means and to the first and second belt brushes to maintain the first and second belt brushes in fore and aft alignment and in a generally oval configuration. The brush belt drive means also causes the drive shaft of the rotating means to rotate the first and second belt brushes in opposing directions. In certain embodiments of the present invention, gear means may be coupled to the drive shaft and to the first and second output shaft in order to alternately rotate the first belt brush in a first direction while maintaining the second belt brush in a substantially fixed position and to rotate the second belt brush in a second direction while maintaining the first belt brush in a substantially fixed position.

DESCRIPTION OF THE DRAWINGS

The invention is pointed out with particularity in the appended claims. However, other objects and advantages together with the operation of the invention may be better understood by reference to the following detailed description taken in connection with the following illustrations wherein:

FIG. 1 is a perspective view of the mechanical toothbrush of the present invention.

FIG. 2 is a perspective view of the transmission assembly of the present invention showing the housing in phantom view;

FIG. 3 is a sectional view of the mechanical toothbrush illustrated in FIG. 1, taken laterally through the brush assembly;

FIG. 4 is a second sectional view of the brush assembly illustrated in FIG. 3, showing the manner in which the first and second bracket sections can be pivotted with respect to each other, and indicating the manner in which the first and second belt brushes of the invention surround and clean a tooth; and FIG. 5 is a sectional view of the mechanical toothbrush illustrated in FIG. 1, taken laterally through the transmission of FIG. 2.

DESCRIPTION OF THE PREFERRED EMBODIMENT

In order to better illustrate the advantages of the invention and its contributions to the art, a preferred hardware embodiment of the invention will now be described in some detail.

Referring now to FIG. 1, the mechanical toothbrush of the present invention includes rotating means in the form of a battery powered electric motor which is enclosed along with an appropriate battery power supply within handle 10. An on/off switch 12 selectively couples and decouples the battery power supply from the electric motor. Brush drive means indicated generally by reference number 14 includes a drive shaft section 15, a transmission 16 and a brush assembly 18.

Referring now to FIGS. 1, 2 and 5, transmission 16 includes a spur gear 20 which is coupled to drive shaft 22 which is rotated by the electric motor. As is best illustrated in FIG. 6, spur gear 20 includes gear teeth only around 180 degrees of its periphery. Spur gear 20 is rotated by drive shaft 22 in a clockwise direction as is illustrated by the arrow in FIG. 5.

Spur gear 20 alternately meshes with the gear teeth of brush drive gear 24 and idler gear 26. As can be seen from FIG. 5, brush drive gear 24 and idler gear 26 are positioned within transmission 16 on diametrically opposite sides of spur gear 20. Gears 24 and 26 have equal diameters and include gear teeth around the complete circumference thereof. As spur gear 20 is continuously rotated in a clockwise direction by drive shaft 22, its gear teeth periodically engage brush drive gear 24, causing it to rotate 180° in a counterclockwise direction. As the gear teeth of spur gear 20 disengage from the gear teeth of brush drive gear 24, they immediately engage the gear teeth of idler gear 26. An additional one hundred and eighty degrees of rotation of spur gear 20 causes idler gear 26 to rotate one hundred and eighty degrees in a counterclockwise direction. Brush drive gear 28 has a depth equal to that of brush drive gear 24 and is positioned in the forward section of transmission 16 as illustrated in FIG. 2 directly beneath the forward section of idler gear 26. Idler gear 26 has a substantially greater depth than the depth of brush drive gears 24 and 28 to permit brush drive gear 28 to be offset to the front of transmission 16 as illustrated in FIG. 2. Brush drive gear 28 includes a plurality of gear teeth around its entire circumference. A complete three hundred and sixty degree revolution of spur gear 20 thus initially causes a one hundred and eighty degree conterclockwise rotation of brush drive gear 24 sequentially followed by a one hundred and eighty degree clockwise rotation of brush drive gear 28. All gears are located within generally cylindrical counterbored sections of transmission 16. Brush drive gears 24 and 28 are coupled to first output shaft 30 and second output shaft 32, respectively. Outputs shafts 30 and 32 include flat end sections and spring biased detent balls 34 and 36 to detachably couple shafts 30 and 32 to brush assembly 18.

Bracket section 36 of brush assembly 18 includes a first idler shaft 40 the fore and aft ends of which are rotatably coupled to the front and rear surfaces of bracket section 36 as illustrated. Similarly, bracket section 38 includes a second idler shaft 42 which is rotatably coupled to the front and rear surfaces of bracket section 36 as illustrated.

First bracket section 36 includes a first loop-shaped, flexible belt brush 44 while second bracket section 38 includes an identical second belt brush 46. Belt brushes 44 and 46 can be fabricated out of any strong, resilient and flexible materials such as nylon. Each of these belt brushes include a plurality of nylon bristles which extend perpendicularly outward from the outer surface of each belt assembly. As is best illustrated in FIG. 3, the relative spacing between output shafts 30 and 32 and idler shafts 40 and 42 are such that the bristles of belt brushes 44 and 46 just meet when bracket sections 36 and 38 are rotated into the closed position illustrated in FIG. 3.

The outer side surfaces 48 and 50 of bracket sections 36 and 38 function as brush guards to prevent the rotating bristles of belt brushes 44 and 46 from contacting the soft tissue of the user's mouth. As can be observed from FIG. 3, the distance between belt brushes 44 and 46 and the innter surface of brush guards 48 and 50 is somewhat less than the length of the bristles of each belt brush. As the belt brushes are rotated in the opposite directions as indicated by the arrows in the lower portion of FIGS. 3 and 4, the bristles of each belt brush are gently compressed by the brush guard section of each bracket section. This bristle compression reduces the outward bristle extension by about one half and permits the overall size of the brush assembly to be significantly reduced facilitating positioning of the brush assembly within the user's mouth. Just prior to the point at which the bristles of a particular belt brush exit the brush guard section of a bracket section, the brush guard flares out to permit the bristles to gradually straighten out and assume a normal full-length configuration.

Coupling means in the form of meshing gear teeth indicated generally by reference numeral 52 forms a part of the rear surface of the brush assembly adjacent to transmission 16. Coupling means 52 causes bracket sections 36 and 38 to symmetrically open and close as the brush assembly is displaced downward over a tooth during the cleaning process as illustrated in FIG. 4. The angled surfaces indicated by reference number 54 of bracket sections 36 and 38 prevent the two bracket sections from being pivotted open beyond a predetermined angle. In FIG. 4, angled surfaces 54 have contacted one another and preclude further outward pivotal motion of bracket sections 36 and 38. The angled surfaces indicated by reference number 56 in FIG. 4 limit the inward pivotal motion of bracket sections 36 and 38 to the position illustrated in FIG. 3 where angled surfaces 56 have contacted one another.

Biasing means in the form of a compression spring 58 is coupled to bracket sections 36 and 38 and serves to bias them to the closed position illustrated in FIG. 3. When the mechanical toothbrush of the present invention is removed from the mouth, spring 58 biases bracket sections 36 and 38 of the brush assembly into the closed position indicated in FIGS. 1 and 3.

The unique configuration of the brush drive means of the present invention permits the lower or brushing section of the brush assembly of the present invention to be spaced apart from the handle 10 and transmission 16 of the present invention in order to substantially facilitate the use of this device. The alternating movement of brush belts 44 and 46 closely simulates the preferred form of manual toothbrushing techniques recommended by dentists.

The rotating belt brush cleans the tooth surface as its bristles move away from the gum line. The idle, non-moving belt brush engages the opposite side of the tooth, resisting the inward pulling force created by the opposing, moving brush. The inward pulling force produced by the moving belt brush slightly displaces the non-moving belt brush toward the gum line causing the non-moving belt brush to massage the gum line. The alternating movement of the two belt brushes prevents the brush assembly from being pulled into excessively close contact with the teeth and gums being cleaned.

Typically, brush belts 44 and 46 not only massage the front and rear gum surfaces but also clean the front, rear and upper surface of an individual's teeth. In order to clean the lower teeth, the mechanical toothbrush of the present invention is positioned as illustrated in FIG. 4. To clean the upper teeth, the handle 10 of the present invention is rotated one hundred and eighty degrees so that the brushing section of brush assembly 18 is positioned above handle 10.

It will be apparent to those skilled in the art that the disclosed mechanical toothbrush may be modified in numerous ways and may assume many embodiments other than the preferred forms specifically set out and described above. For example, transmission 16 has been designed to produce unique sequentially alternating displacements of belt brushes 44 and 46. In certain instances, it may be desirable to provide a substantially simplified transmission which merely causes brush belts 44 and 46 to simultaneously rotate in opposing directions or to be displaced in some other sequence. The redesign of transmission 16 to accomplish these different objectives could be readily accomplished by one skilled in the art. Similarly, the specific housing configuration and relative dimensions of the brush assembly including the brush belts could be readily modified without substantially departing from the scope of the present invention. Accordingly, it is intended by the appended claims to cover all such modifications of the invention which fall within the true spirit and scope of the invention.

I claim:
1. A mechanical toothbrush comprising:
 a. means for rotating a drive shaft;
 b. a first loop-shaped belt brush; and
 c. a second loop-shaped belt brush; and
 d. brush drive means coupled to said rotating means and to said first and second belt brushes for maintaining said first and second belt brushes in fore and aft alignment and in an oval configuration and for causing said drive shaft to rotate said first and second belt brushes in opposing directions.

2. The mechanical toothbrush of claim 1 wherein said brush drive means includes transmission means coupled to said rotating means for converting the rotary motion of said drive shaft into opposing rotary motion of first and second parallel oriented, spaced apart output shafts.

3. The mechanical toothbrush of claim 2 wherein said brush drive means further includes bracket means coupled to said transmission means for maintaining a first idler shaft at a predetermined distance from said first output shaft and for maintaining a second idler shaft at a predetermined distance from said second output shaft.

4. The mechanical toothbrush of claim 3 wherein said first belt brush is looped around said first output shaft and said first idler shaft and is rotated in a first direction by said transmission means and wherein said second belt brush is looped around said second output shaft and said second idler shaft and is rotated in a second direction by said transmission means.

5. The mechanical toothbrush of claim 4 wherein said bracket means includes first and second bracket sections and wherein said first idler shaft is coupled to said first bracket section and said second idler shaft is coupled to said second bracket section.

6. The mechanical toothbrush of claim 5 wherein said first and second bracket sections are pivotally coupled to said transmission means to permit said first idler shaft to be rotated with respect to said first output shaft and to permit said second idler shaft to be rotated with respect to said second output shaft.

7. The mechanical toothbrush of claim 6 further including coupling means coupled to said first and second bracket sections for causing rotational displacements of either one of said first or second bracket sections to produce corresponding symmetrical displacements of said other bracket section.

8. The mechanical toothbrush of claim 6 further including biasing means coupled to said first and second bracket sections for biasing said first and second bracket sections to maintain a minimum spacing between said first and second idler shafts.

9. The mechanical toothbrush of claim 8 wherein said biasing means includes a spring coupled to said first and second bracket sections.

10. The mechanical toothbrush of claim 1 wherein said rotating means includes an electric motor.

11. The mechanical toothbrush of claim 10 wherein said electric motor is battery powered.

12. The mechanical toothbrush of claim 1 wherein said first and second belt brushes are fabricated from a flexible material and include a plurality of outward facing bristles.

13. The mechanical toothbrush of claim 2 wherein said first and second belt brushes are fabricated from nylon.

14. The mechanical toothbrush of claim 2 wherein said transmission means includes gear means coupled to said drive shaft and to said first and second output shafts for alternately rotating said first belt brush in a first direction while maintaining said second belt brush in a substantially fixed position and for rotating said second belt brush in a second direction while maintaining said first belt brush in a substantially fixed position.

15. The mechanical toothbrush of claim 14 wherein said gear means includes a spur gear coupled to said drive shaft and having one hundred and eighty degrees of gear teeth around the periphery thereof.

16. The mechanical toothbrush of claim 5 wherein the opposing surfaces of said first and second belt brushes form a brushingg region for cleaning the exterior surfaces of a tooth.

17. The mechanical toothbrush of claim 16 wherein said first and second bracket sections each include a brush guard for forming a barrier between the moving bristles of said first and second belt brushes and the interior surfaces of a user's mouth.

18. The mechanical toothbrush of claim 17 wherein said brush guard is positioned closer to said first and second belt brushes than the length of the bristles in said first and second belt brushes to compress the bristles.

19. A mechanical toothbrush comprising:
 a. means for rotating a drive shaft;
 b. transmission means coupled to said rotating means for converting the rotary motion of said drive shaft into opposing rotary motion of first and second parallel oriented, spaced apart output shafts; and
 c. a brush assembly including
  i. bracket means coupled to said transmission means for maintaining a first idler shaft at a predetermined distance from said first output shaft and for maintaining a second idler shaft at a predetermined distance from said second output shaft
  ii. a first belt brush looped around said first output shaft and said first idler shaft and rotated in a first direction by said transmission means
  iii. a second belt brush looped around said second output shaft and said second idler shaft and rotated in a second direction by said transmission means;
whereby rotational motion of said drive shaft causes said first and second belt brushes to rotate in opposite directions.

20. The mechanical toothbrush of claim 19 wherein said transmission means includes gear means coupled to said drive shaft and to said first and second output shafts for alternately rotating said first belt brush in a first direction while maintaining said second belt brush in a substantially fixed position and for rotating said second belt brush in a second direction while maintaining said first belt brush in a substantially fixed position.

21. The mechanical toothbrush of claim 20 wherein said gear means includes a spur gear coupled to said drive shaft and having one hundred and eighty degrees of gear teeth around around the periphery thereof.

22. The mechanical toothbrush of claim 19 wherein said bracket means includes first and second bracket sections and wherein said first idler shaft is coupled to said first bracket section and said second idler shaft is coupled to said second bracket section.

23. The mechanical toothbrush of claim 22 wherein said first and second bracket sections are pivotally coupled to said transmission means to permit said first idler shaft to be rotated with respect to said first output shaft and to permit said second idler shaft to be rotated with respect to said second output shaft.

24. The mechanical toothbrush of claim 23 further including means connected to said first and second bracket sections for causing rotational displacements of either one of said first or second bracket sections to produce corresponding symmetrical displacements of said other bracket section.

25. The mechanical toothbrush of claim 24 further including biasing means coupled to said first and second bracket sections for biasng said first and second sections to maintain a minimum spacing between said first and second idler shaft.

26. The mechanical toothbrush of claim 25 wherein said biasing means includes a spring.

* * * * *